US008079988B2

(12) United States Patent
Beechie (10) Patent No.: US 8,079,988 B2
(45) Date of Patent: Dec. 20, 2011

(54) ENEMA DEVICE

(75) Inventor: Kenneth L. Beechie, University Place, WA (US)

(73) Assignee: The Beechie Company, University Place, WA (US)

( * ) Notice: Subject to any disclaimer, the term of this patent is extended or adjusted under 35 U.S.C. 154(b) by 0 days.

(21) Appl. No.: 12/815,135

(22) Filed: Jun. 14, 2010

(65) Prior Publication Data

US 2010/0249730 A1      Sep. 30, 2010

Related U.S. Application Data (63) Continuation-in-part of application No. 12/040,545, filed on Feb. 29, 2008, now abandoned.

(60) Provisional application No. 60/892,465, filed on Mar. 1, 2007.

(51) Int. Cl.
*A61M 31/00*      (2006.01)

(52) U.S. Cl. ......... 604/275; 604/278; 604/279; 604/911

(58) Field of Classification Search ............... 604/36, 604/37, 187, 212, 257, 275–279, 911, 514–517
See application file for complete search history.

(56) References Cited

U.S. PATENT DOCUMENTS

| | | | | |
|---|---|---|---|---|
| 925,718 | A * | 6/1909 | Pearl | 604/248 |
| 3,469,571 | A * | 9/1969 | Vass | 600/431 |
| 5,250,024 | A | 10/1993 | Kensey | |
| 5,380,275 | A | 1/1995 | Kensey | |
| 6,110,150 | A | 8/2000 | Singo | |
| 6,632,195 | B1 | 10/2003 | Smith | |
| 2003/0195481 | A1 | 10/2003 | Xu | |
| 2005/0038374 | A1 | 2/2005 | Williams, Jr. | |

OTHER PUBLICATIONS

Office Action mailed Dec. 3, 2008, from U.S. Appl. No. 12/040,545, filed Feb. 29, 2008.
Final Office Action mailed Jun. 2, 2009, from U.S. Appl. No. 12/040,545, filed Feb. 29, 2008.
Office Action mailed Sep. 11, 2009, from U.S. Appl. No. 12/040,545, filed Feb. 29, 2008.
Final Office Action mailed Mar. 1, 2010, from U.S. Appl. No. 12/040,545, filed Feb. 29, 2008.

* cited by examiner

*Primary Examiner* — Kevin C Sirmons
*Assistant Examiner* — Kami A Bosworth
(74) *Attorney, Agent, or Firm* — Christensen O'Connor Johnson Kindness PLLC (57) ABSTRACT

An enema device for use with a source of enema fluid having an elongated nozzle includes a hollow elongated rigid body having an interior extending between first and second ends and a feed portion formed at the first end defining a feed portion opening. A hollow nozzle receiving portion extends from the feed portion opening and is in fluid communication with the feed portion opening and the interior of the hollow elongated body. The hollow nozzle receiving portion is sized and configured to slidably receive the elongated nozzle, wherein when the elongated nozzle is slidably received within the hollow nozzle receiving portion, the elongated nozzle is in fluid communication with the interior of the hollow elongated body. The enema device further includes a discharge portion disposed at the second end of the elongated body. The discharge portion defines a discharge opening in communication with the interior of the hollow elongated body.

11 Claims, 8 Drawing Sheets

ENEMA DEVICE

CROSS-REFERENCES TO RELATED APPLICATIONS

This application is a continuation-in-part of U.S. application Ser. No. 12/040,545, filed Feb. 29, 2008, which claims the benefit of U.S. Provisional Application No. 60/892,465, filed on Mar. 1, 2007, the disclosures of which are hereby expressly incorporated by reference.

BACKGROUND

An enema is a common medical procedure whereby fluid is injected into the rectum of a patient in order to induce bowel movement. The need for such a procedure typically arises in patients suffering from certain physical ailments in which voluntary bowel control is impaired.

Medical equipment currently exists in the art for administering an enema to patients in need of this medical procedure. At least one type of equipment consists of an enema squeeze bottle filled with the fluid intended to induce bowel movement, which is capped by a short applicator nozzle to be inserted into the patient's rectum. The applicator nozzle of this type of conventional enema application device often causes discomfort and irritation when being inserted. Therefore, it is desired to have an enema device that safely and effectively administers the enema to a patient without causing discomfort.

Moreover, enemas are often administered to a patient at home when the need for medical assistance does not necessitate a doctor or another health care assistant. However, it is often difficult for the patient to administer the enema to him or herself since the applicator nozzle must be inserted into such a small, sensitive area. Moreover, it is difficult for the patient to administer the fluid while steadily holding the enema in the required area. Often the patient is assisted by another individual; however, assistance may not always be available, if, for instance, the patient lives alone. Thus, there is also a need for an enema device that can be effectively self-administered.

SUMMARY

An enema device for use with a source of enema fluid having an elongated nozzle includes a hollow elongated rigid body having an interior extending between first and second ends and a feed portion formed at the first end defining a feed portion opening. A hollow nozzle receiving portion extends from the feed portion opening and is in fluid communication with the feed portion opening and the interior of the hollow elongated body. The hollow nozzle receiving portion is sized and configured to slidably receive the elongated nozzle, wherein when the elongated nozzle is slidably received within the hollow nozzle receiving portion, the elongated nozzle is in fluid communication with the interior of the hollow elongated body. The enema device further includes a discharge portion disposed at the second end of the elongated body. The discharge portion defines a discharge opening in communication with the interior of the hollow elongated body.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of the present disclosure will become more readily appreciated by reference to the following detailed description, when taken in conjunction with the accompanying drawings, wherein.

DETAILED DESCRIPTION

Figure 1:
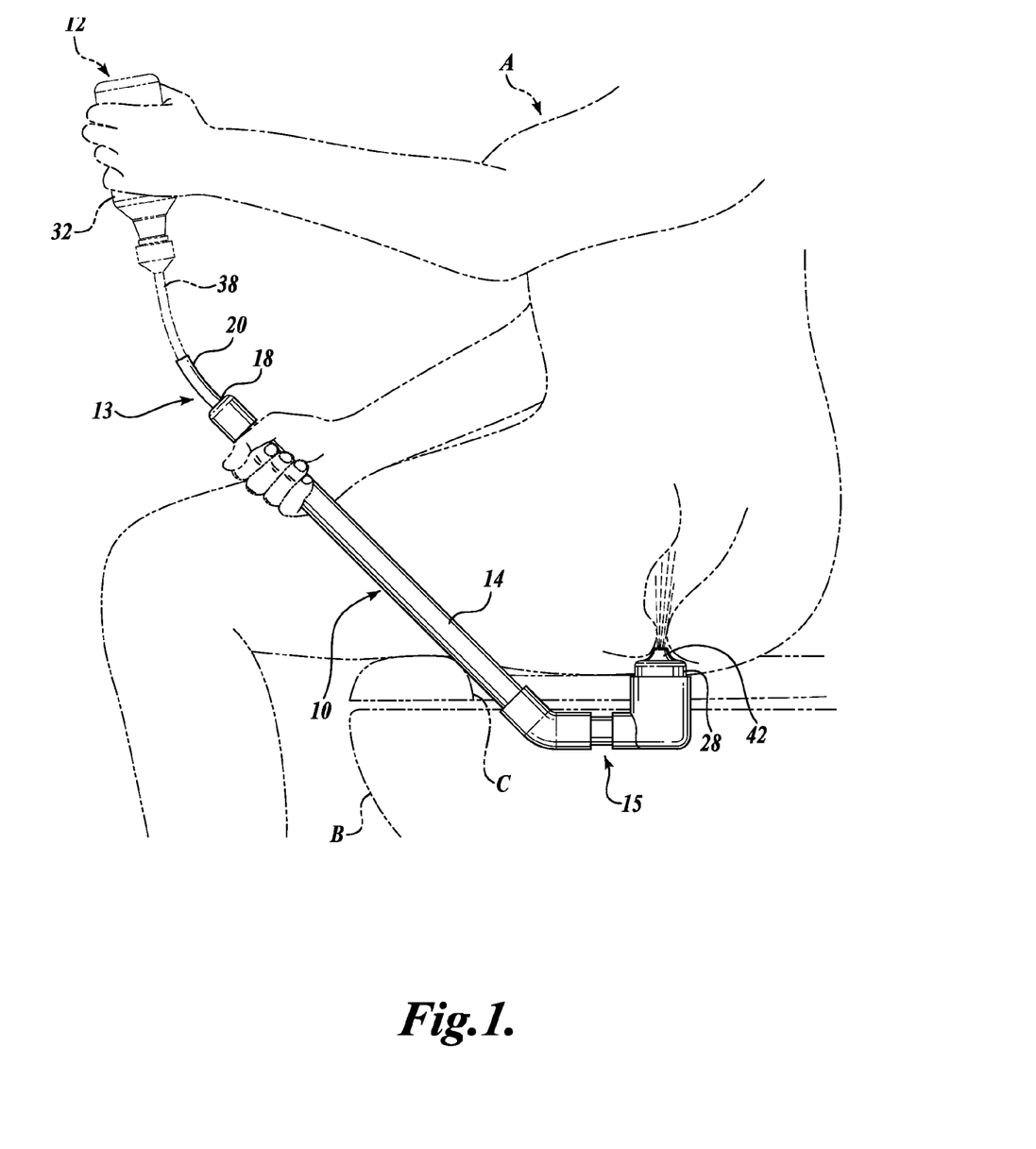
FIG. 1 is an environmental view of an enema device constructed in accordance with one embodiment of the present disclosure, wherein the enema device is shown in use with a pre-packaged enema bottle.

An enema device 10 shown in accordance with one embodiment of the present disclosure is best seen by referring to FIG. 1, wherein the enema device is being used by a patient A sitting on a toilet B. The enema device 10 is shown in use with a prepackaged disposable enema 12 that contains a suitable medicated fluid used for enemas. It should be appreciated that the enema device 10 may instead be used with any suitable enema, such as an enema bag or a bulb syringe. The enema device 10 may be used by a patient A to self-administer the enema when sitting on the toilet B; however, the patient A may instead be standing or sitting in any suitable position such that the enema device 10 may effectively be used.

Figure 2:
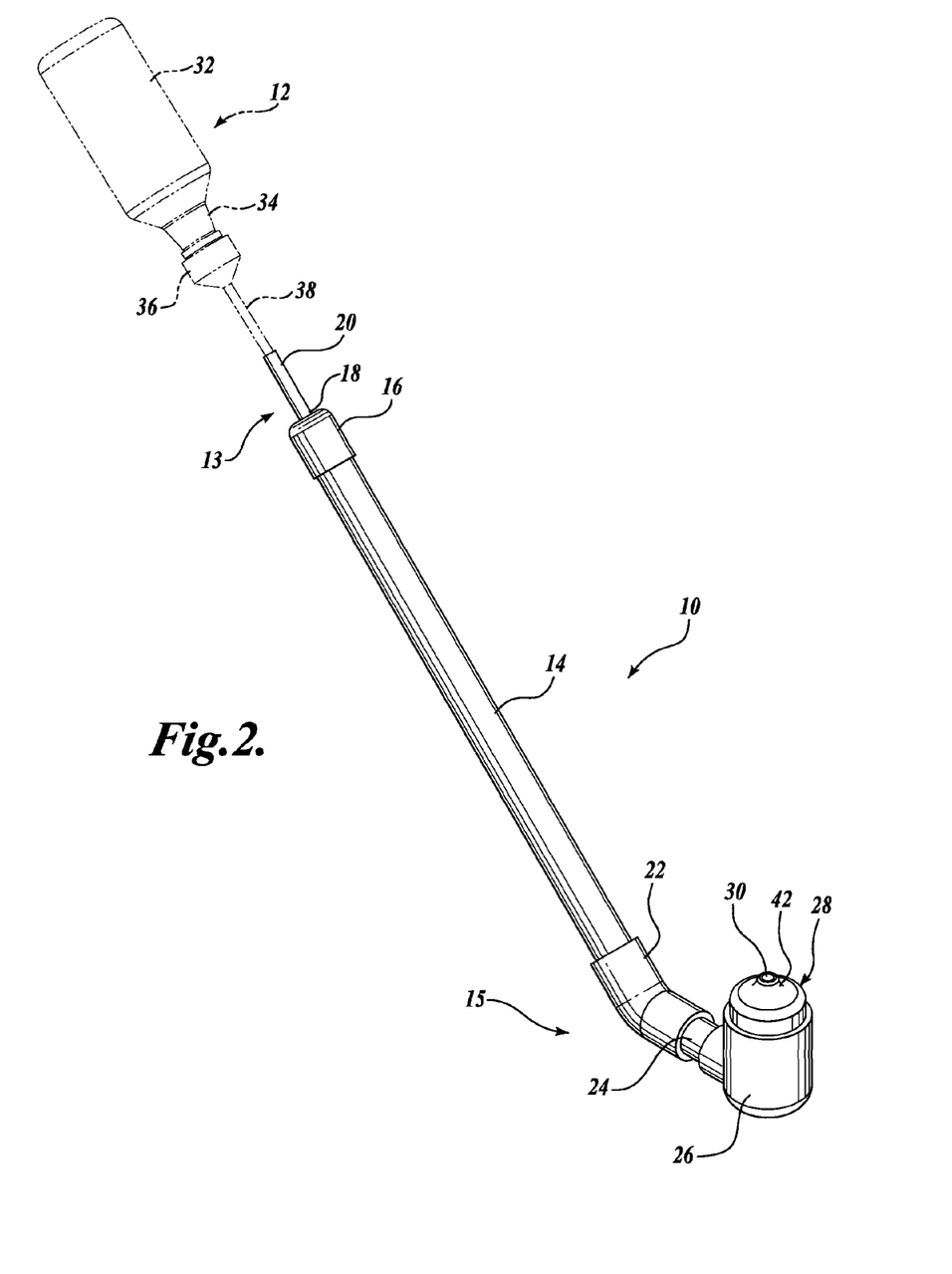
FIG. 2 is an isometric view of the enema device of FIG. 1.
Figure 3:
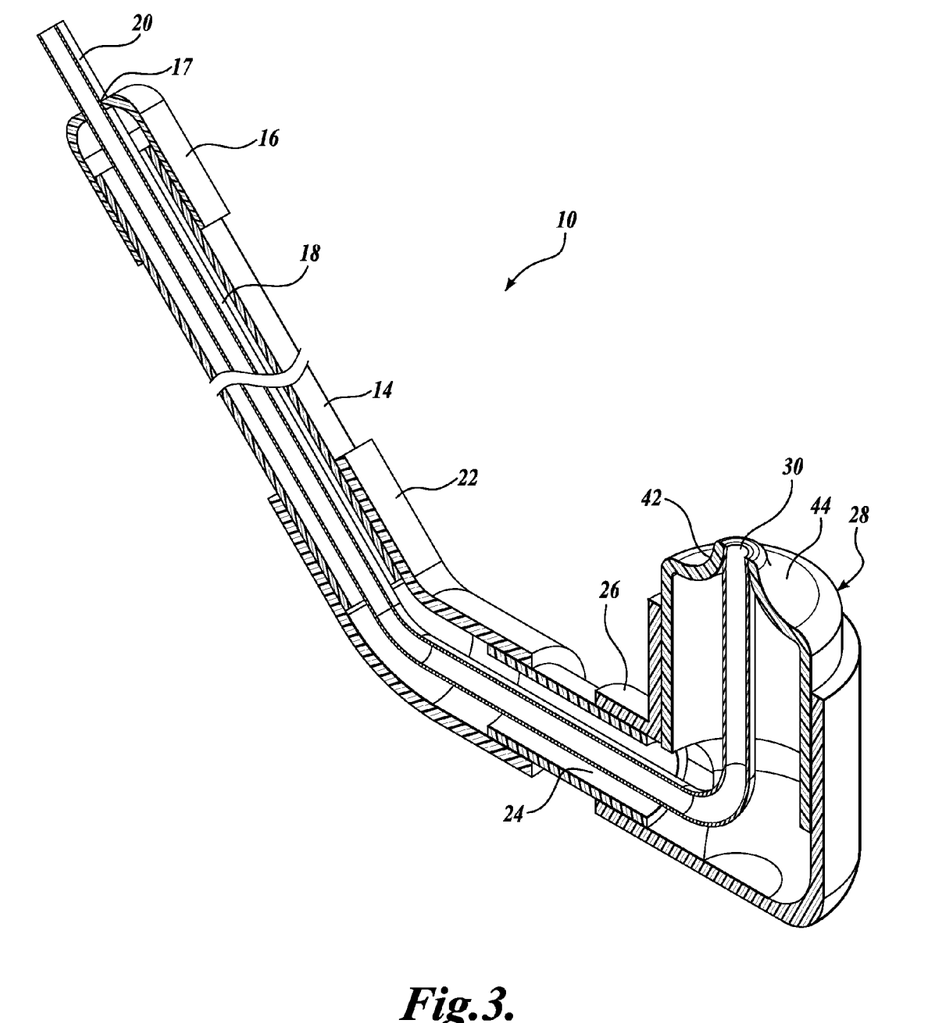
FIG. 3 is a cross-sectional isometric view of the enema device of FIG. 2.

Referring to FIGS. 2 and 3, the enema device 10 includes a hollow, rigid elongated body 14 that acts as a lever against the toilet B or another suitable abutment device to brace the lower enema device 10 against the patient's buttocks (see FIG. 1). The elongated body 14 is preferably circular in cross section or any other suitable cross sectional shape. The elongated body 14 is substantially straight such that it acts as a suitable lever against the toilet B; however, it should be appreciated that the elongated body 14 may instead be suitably curved or contoured to position the enema device 10 against the front interior portion C of a toilet B or similar device. Moreover, an adjustable brace (not shown) may also be received on the elongated body 14 to help position and maintain the elongated body 14 against the front interior portion C of a toilet B. The elongated body 14 may also include a telescoping feature (not shown) that would allow the patient to lengthen or shorten the enema device 10 as needed. The elongated body 14 is preferably made of any suitable rigid material, such as polyvinyl chloride (PVC).

The enema device 10 includes a feed portion 13 disposed at the upper end of the elongated body 14 that is adapted to engage the prepackaged enema 12 and receive the medicated fluid from the prepackaged enema 12. The feed portion 13 includes a hollow cap 16 that is tightly received on the upper end of the elongated body 14 to enclose the upper end of the elongated body 14. The cap 16 includes a relatively small opening 17 in substantially the center of the cap that is adapted to receive a transport tube 18. The transport tube 18 is preferably made of a flexible material, such as rubber, and it extends throughout the length of the elongated body 14 and upwardly and outwardly from the cap 16 through the opening 17. The protruding portion of the transport tube 18 defines a feed tube portion 20 that is of a length and diameter to tightly receive, for instance, a nozzle 38 of the prepackaged enema 12 within the upper end of the feed tube portion 20.

It should be appreciated that the transport tube 18 may instead receive a separate feed tube (not shown) thereon that is adapted to receive the nozzle 38 of the prepackaged enema 12. The feed tube could be made of a flexible or semi-flexible material, such as rubber, and may be of a suitable length to act as an extension of the enema device 10 and facilitate easy insertion of the nozzle 38 within the feed tube at a desired distance from the enema device 10 or by another person.

In an alternative configuration, the transport tube 18 may not utilize a feed tube portion 20. Rather, a tapered opening may be formed in the cap 16 for receiving the nozzle 38 of the prepackaged enema 12. Such opening is tapered to receive nozzles 38 of various sizes. In this configuration, the tube 18 is in fluid flow communication with the tapered opening formed in the cap 16.

The enema device 10 further includes an applicator portion 15 disposed at the lower end of the elongated body 14 that is adapted to position the enema device 10 against the buttocks of the patient A for application of the enema. The applicator portion 15 includes a first elbow fitting 22 that is tightly received at one end on the lower end of the elongated body 14. The first elbow fitting 22 preferably includes only a slight bend such that an obtuse angle is formed between the elongated body 14 and the first elbow fitting 22. A sleeve fitting 24 is tightly received within the other end of the first elbow fitting 22, and a second elbow fitting 26 is tightly received on the sleeve fitting 24. The second elbow fitting 26 includes a substantially horizontal portion that is secured to the sleeve fitting 24 and a substantially vertical portion that defines a circular opening adapted to receive an end cap 28 therewithin.

The end cap 28 is circular in cross section and includes curved or contoured edges such that it is comfortably received against the patient's buttocks. The end cap 28 includes an end face 44 having a discharge opening 30 formed in substantially the center of the end face 44 that is adapted to receive the lower end of the transport tube 18 tightly therewithin. The transport tube 18 is positioned within the opening 30 such that the end of the tube 18 is substantially flush with the end face 44 of the end cap 28.

Preferably, the end cap 28 is contoured to help align the opening 30 against the patient's rectum and provide comfort to the patient A during use. Any suitable end cap shape may be used. As a non-limiting example, the end cap 28 may include a self-centering upward protrusion 42 formed around the opening 30, as shown in FIGS. 1-3. The self-centering upward protrusion 42 may be any suitable contoured shape to engage the opening of the rectum. For instance, the end face 44 may be slightly concave and extend upwardly toward the opening 30 to define the self-centering protrusion 42 and provide a soft, curved engagement surface. The self-centering protrusion 42 may instead be a small dome (not shown) formed on a substantially flat end face 44.

In the alternative configuration of cap 16 discussed above, the nozzle 38 of the enema bottle cap 36 is conveniently engaged within the tapered opening formed in cap 16 of the device feed portion 13. It will be appreciated that the cap 16 may be formed with a thicker or alternative configuration end portion than shown in FIG. 3, so as to provide sufficient length for the tapered opening formed therein. Once the nozzle 38 is engaged within such tapered opening, the prepackaged enema 12 is placed in secure fluid communication with the enema device 10.

Figure 4:
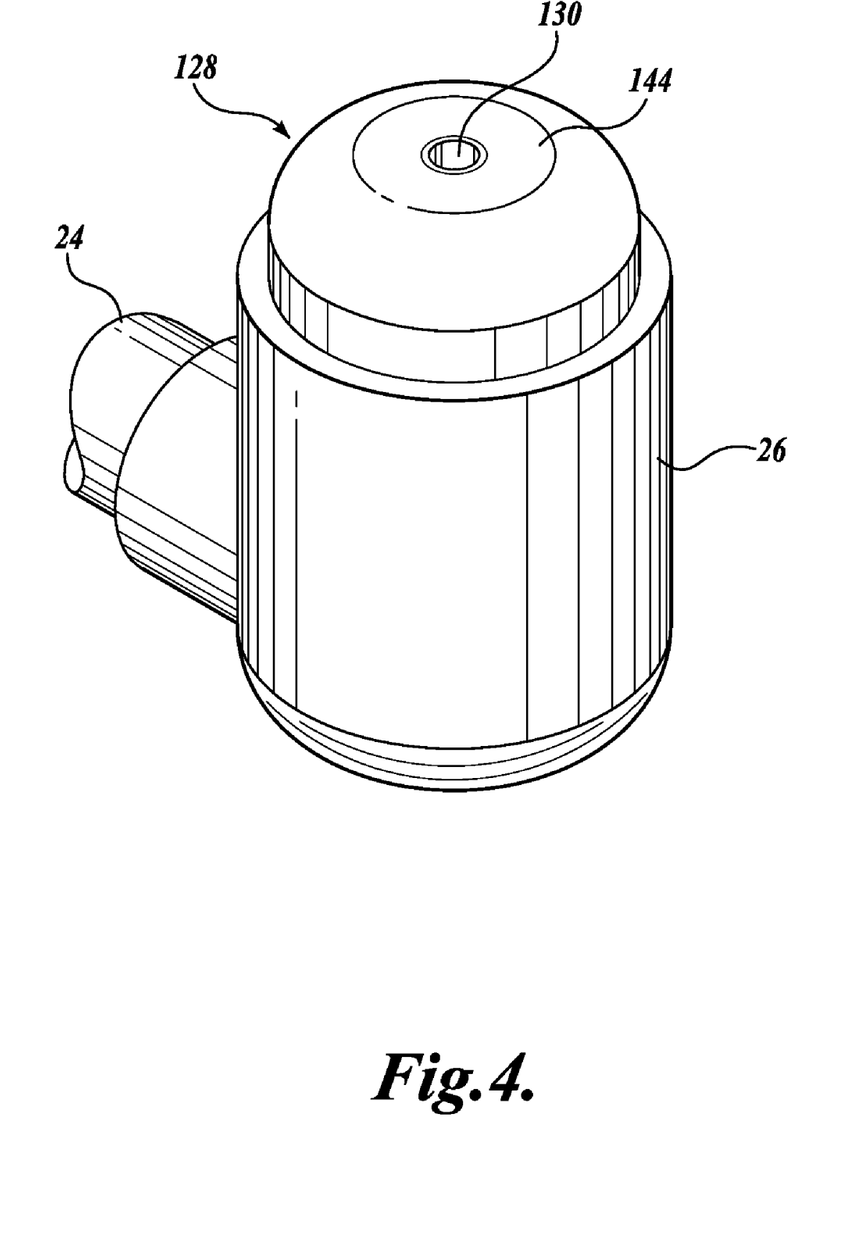
FIG. 4 is a first alternate embodiment of a portion of the enema device of FIG. 2.

FIG. 4 depicts a first alternate embodiment of an end cap 128, wherein the end cap 128 includes a substantially flat end face 144 with an opening 130 formed therein. The end cap 128 includes a curved perimeter edge to provide a contoured engagement surface.

Figure 5:
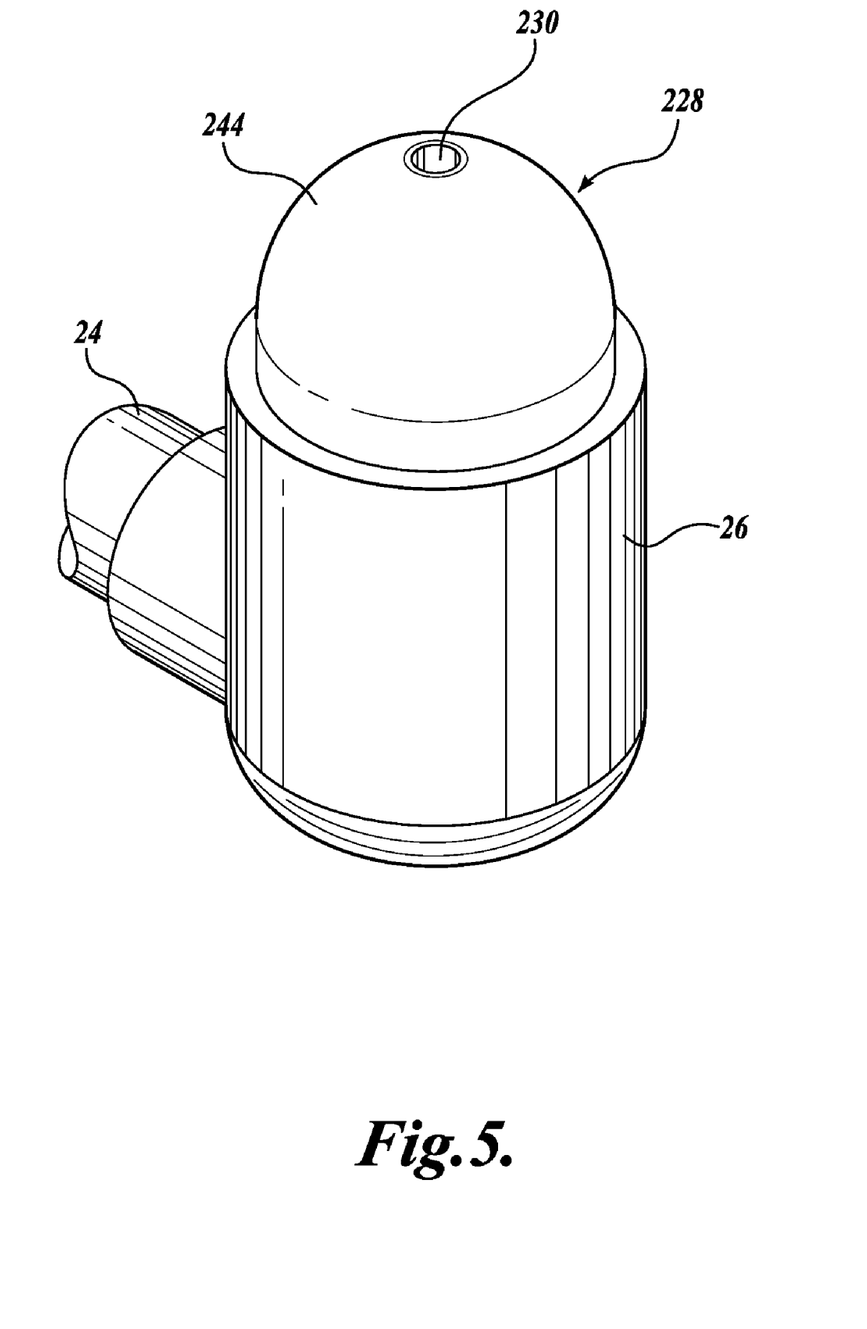
FIG. 5 is a second alternate embodiment of a portion of the enema device of FIG. 2.

FIG. 5 depicts a second alternate embodiment of an end cap 228, wherein the end cap 228 includes a convex, dome surface 244 having a central opening 230 formed therein. It should be appreciated that any suitable contoured end cap shape may instead be used. Moreover, the end cap 28 may be any suitable cross-sectional shape, such as round, elliptical, etc.

Although the enema device 10 has been illustrated and described as having many different parts, it should be appreciated that the rigid components of the enema device 10 (i.e. the cap 16, elongated body 14, first elbow fitting 22, sleeve fitting 24, second elbow fitting 26, and end cap 28) may instead be formed together as one hollow piece formed by injection molding or another suitable method. Moreover, the enema device 10 may be any suitable shape such that it may effectively be used to administer an enema, as described below. Furthermore, the enema device 10 need not include a transport tube 18. Rather, the medicated fluid may instead be received and transported within the rigid components of the enema device 10.

Referring to FIG. 2, the feed portion 13 of the enema device 10 is adapted to receive the medicated fluid from the prepackaged disposable enema 12 or any other suitable enema. The prepackaged disposable enema 12 preferably includes an enema bottle 32 having a threaded bottle neck 34 that receives a twist-on threaded bottle cap 36. The enema bottle 32 is preferably prefilled with a medicated fluid that is well known in the art. The upper end of the bottle cap 36 includes an opening that is in communication with a nozzle 38 secured to the bottle cap 36. The nozzle 38 is adapted to be tightly received within the feed tube portion 20 of the transport tube 18 to place the prepackaged enema 12 into fluid communication with the enema device 10.

Figure 6:
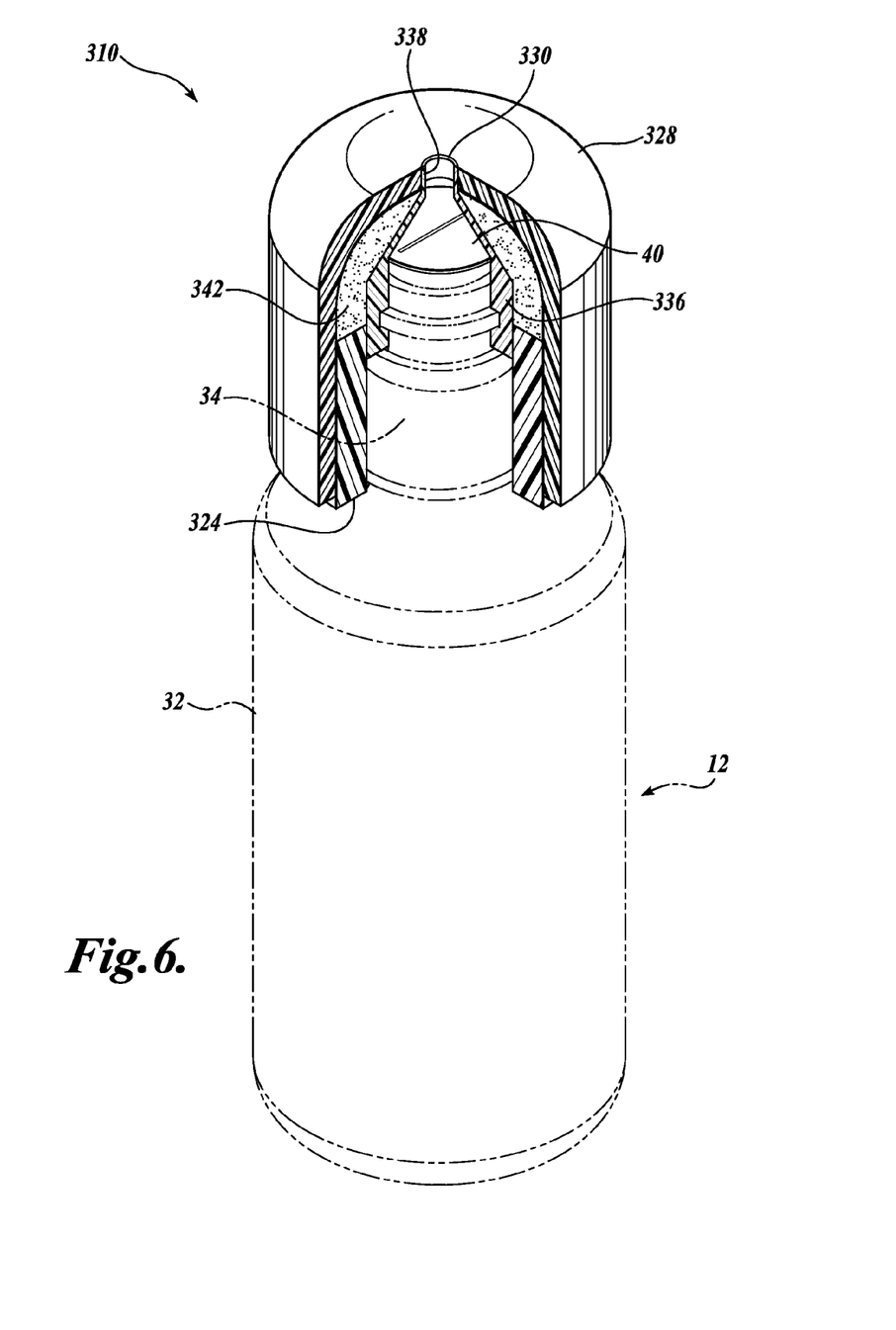
FIG. 6 is a partial cross-sectional view of a first alternate embodiment of an enema device, wherein the enema device is shown in use with a pre-packaged enema bottle.

As can best be seen be referring to FIG. 6, the bottle cap 36 includes a one-way anti-reflux valve 40 that is positioned within the bottle cap 36 such that it encloses the opening in the bottle neck 34. The one-way valve 40 is preferably made from a non-porous flexible material and can be circular in shape, and is of a size which permits accommodation into the bottle cap 36. The one-way valve 40 prevents reflux of the medicated fluid back up into the bottle 32, thereby holding back any contaminants as well as helping to sustain the collapsibility of the bottle 32.

Referring to FIG. 1, the enema device 10 is most easily used when the patient is seated on a toilet B. To use the enema device 10, the patient A positions the applicator portion 15 beneath his or her buttocks such that a portion of the elongated body 14 and the feed portion 13 extend upwardly and outwardly from the toilet B in front of the patient A. The patient A then positions the end cap 28 properly against the rectum such that the self-centering protrusion 42 is received therein and the opening 30 is in fluid communication therewith.

The patient A thereafter pushes the top portion of the elongated body 14 outwardly to engage the elongated body 14 on the front interior portion C of the toilet B and pivot the elongated body 14 on the front interior portion C. The top portion of the elongated body 14 is pushed outwardly until the end cap 28 is firmly engaged against the rectum. While holding the enema device 10 in this position, the patient inserts the nozzle 38 of the prepackaged enema 12 into the feed tube 20. The patient A then squeezes the bottle 32 to force the medicated fluid out of the valve 40, through the nozzle 38, and into the transport tube 18. The fluid travels forcibly down through the transport tube 18 until it reaches the opening 30 in the end cap 28. The medicated fluid exits the opening 30 and projects upwardly into the patient's rectum. In this manner, the patient is able to administer an enema without the help of another person, and without inserting an uncomfortable tip into the rectum. However, it should be appreciated that the enema device 10 may instead be used with the assistance of a second person.

Now referring to FIG. 6, an alternate embodiment of an enema device 310 includes an end cap 328 that is adapted to be received onto the bottle neck 34 of a disposable enema bottle 32. The enema device 310 includes a sleeve fitting 324 that is adapted to be received over the lower portion of the bottle neck 34. An end cap 328, substantially similar in shape and size to the end cap 28 of the enema device 10 is tightly received over at least a portion of the sleeve fitting 324.

The end cap 328 and sleeve fitting 324 are adapted to receive a cap 336 and nozzle 338 substantially similar to the cap 36 and nozzle 38 that come with the prepackaged enema 12 except that the nozzle 338 is shorter in length. The end cap 328 includes an opening 330 that is adapted to receive at least a portion of the tip 338 such that the tip 338 does not protrude from the opening 330 of the end cap 328, or is otherwise flush with the exterior surface of the end cap 328.

The cap 336 and tip 338 are secured within the sleeve fitting 324 and the end cap 328 by first filling the upper portion of the cap 328 with an epoxy or thermosetting material 342 and thereafter press fitting the cap 336 and tip 338 therewithin. The tip 338 is received within the opening 330 and the cap 336 is secured within the upper end of the interior of the end cap 328. The sleeve 324, cap 336, tip 338, and end cap 328 cooperatively define the enema device 310. The enema device 310 replaces the standard cap 36 and nozzle 38 that comes attached to the bottle 32 of the prepackaged enema 12. It should be appreciated that the enema device 310 may be instead made in any other suitable manner.

To use the enema device 310, the patient first removes the cap 36 that is attached to the bottle 32 of the prepackaged enema 12. The patient then secures the enema device 310 to the bottle 32 by inserting the threaded portion of the bottle neck 34 into the cap 336 and thereafter twisting the end cap 328. The patient then positions the enema device 310 such that the end cap 322 abuts the buttocks and the opening 330 is aligned with the rectum. While holding the bottle 32 and enema device 310 in this position, the patient then squeezes the bottle 32 to force the medicated liquid out of the one-way valve 40, through the tip 338, and outwardly through the opening 330 of the enema device 310 into the patient's rectum. Although the enema device 310 can be used to self-administer the enema, it is preferred that another person positions the enema device 310 and administers the enema to the patient.

Figure 7:
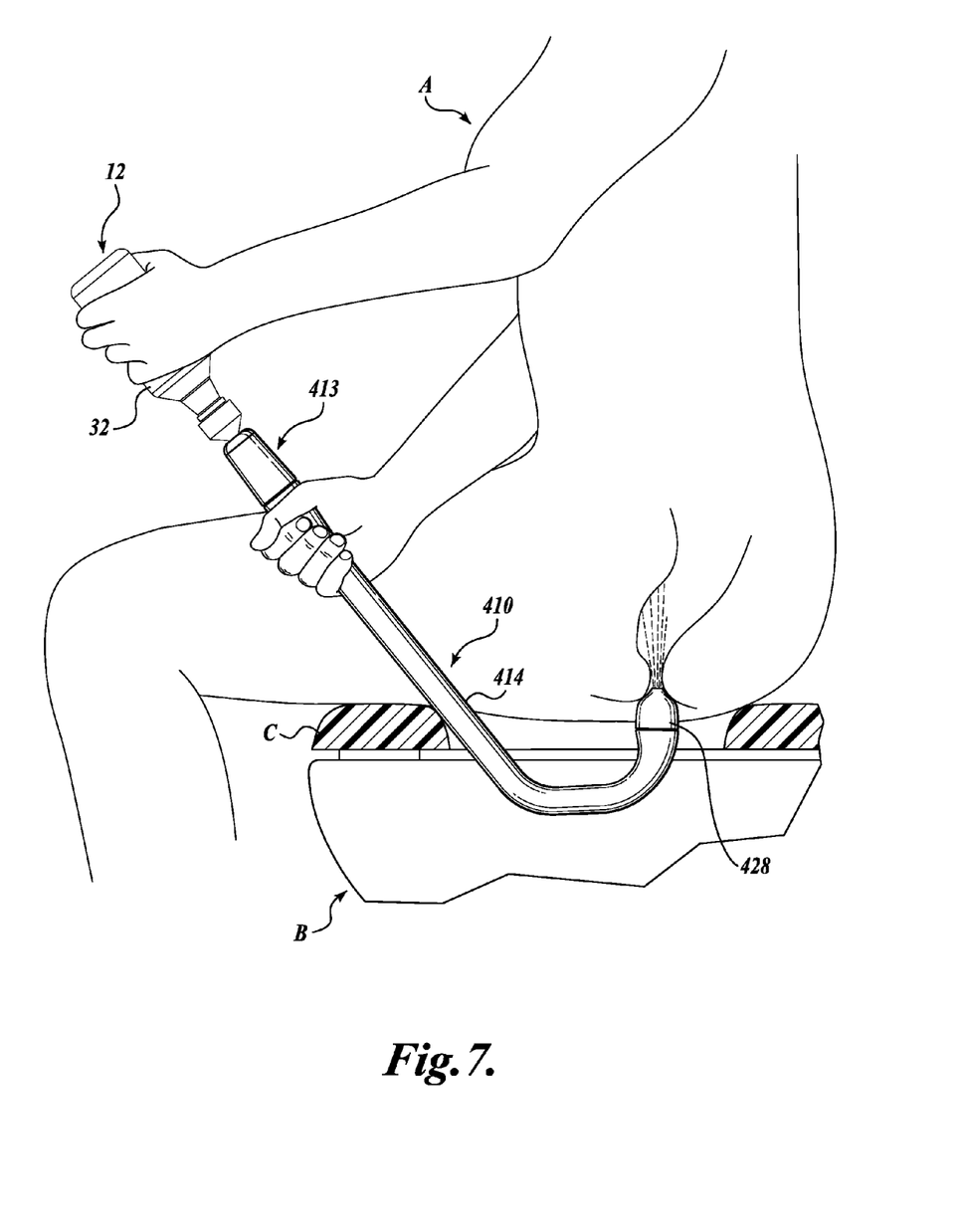
FIG. 7 is an environmental view of a second alternate embodiment of an enema device, wherein the enema device is shown in use with a pre-packaged enema having an elongated nozzle.

Referring to FIG. 7, an alternate embodiment of an enema device 410 for use with a source of enema fluid is depicted. The enema device 410 is substantially similar to enema device 10; and therefore, the enema device 410 can be used in a substantially similar manner as that described above with reference to the enema device 10. In that regard, the enema device 410 is shown being used by a patient A sitting on a toilet B. The enema device 410 may be used with a prepackaged disposable enema 12, as described above, or any other suitable enema, such as an enema bag or a bulb syringe. The enema device 410 may be used by a patient A to self-administer the enema when sitting on the toilet B; however, the patient A may instead be standing or sitting in any suitable position such that the enema device 410 may effectively be used.

Figure 8:
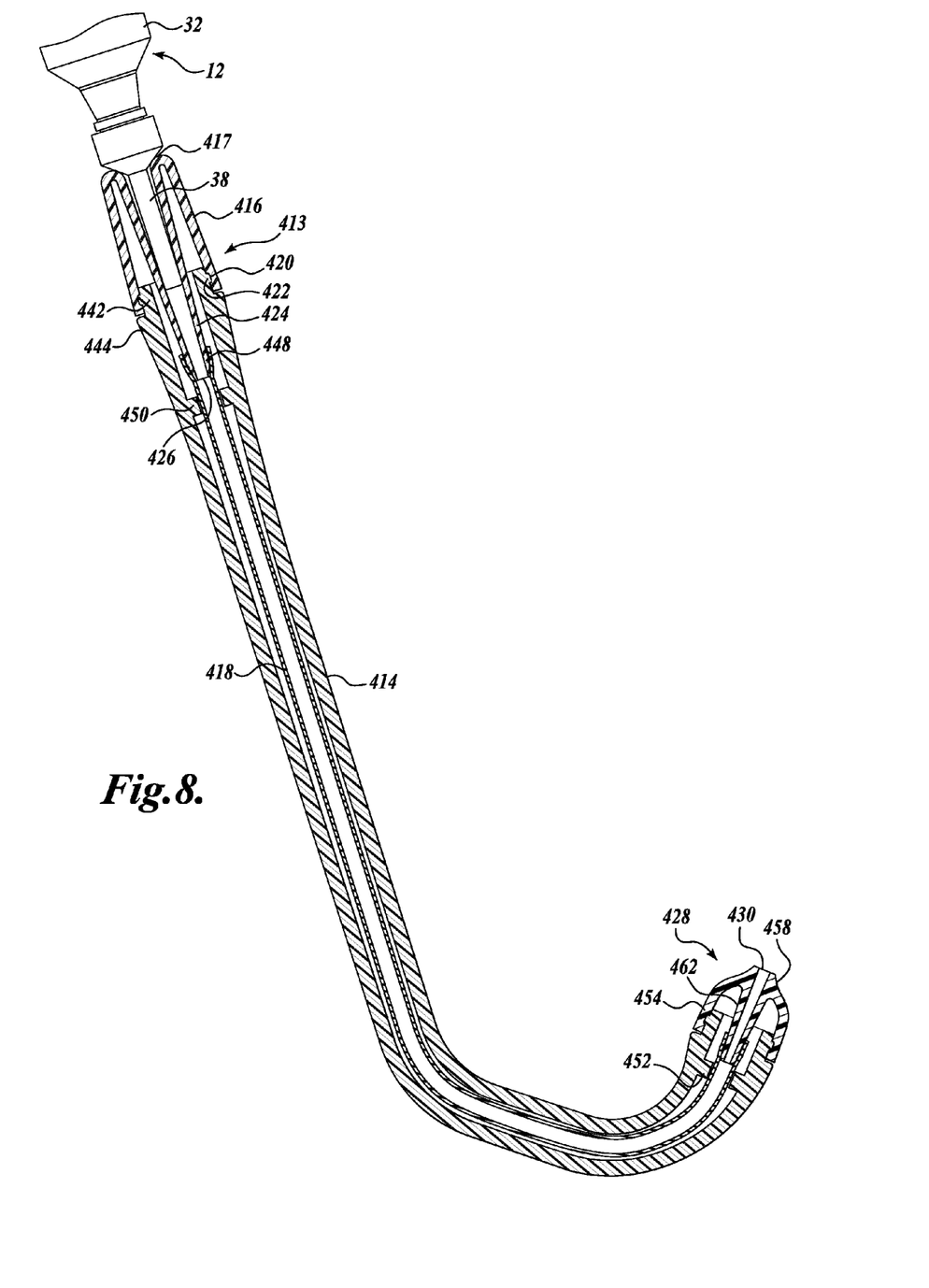
FIG. 8 is a cross-sectional side view of the enema device of FIG. 7.

Referring to FIGS. 7 and 8, the enema device 410 includes a hollow, rigid, elongated body 414 that includes a substantially straight portion and a curved portion to define an overall J-shape. The straight portion of the elongated body 414 acts as a lever against the toilet B or another suitable abutment device to brace the distal curved portion against the patient's buttocks. It should be appreciated that the elongated body 414 may instead be any suitable contour to help position and temporarily secure the enema device 410 against the front interior portion C of a toilet B or similar device. Furthermore, the elongated body 414 is preferably circular in cross section or any other suitable cross sectional shape and is made from a suitable rigid material, such as polyvinyl chloride (PVC).

The enema device 410 includes a feed portion 413 disposed at the upper, proximal end of the straight portion of the elongated body 414 that is adapted to engage the prepackaged enema 12 and receive the medicated fluid from the prepackaged enema 12. The feed portion 413 includes a hollow cap portion 416 that is tightly and securely received on the upper end of the elongated body 414 to enclose the upper end of the elongated body 414. Although the cap portion 416 may be secured on the upper end of the elongated body 414 in any suitable manner, the hollow cap portion 416 preferably includes an interior annular groove 420 that is mateable with a correspondingly shaped annular protrusion 422 formed on the exterior of the upper end of the elongated body 414.

The feed portion 413 is preferably made from a resiliently deformable material, such as rubber or plastic, such that the cap portion 416 may expand to fit over the upper end of the elongated body 414 until the interior annular groove 420 is received over the annular protrusion 422. As such, the feed portion 413 may be detached from the elongated body 414 for cleaning, repair, etc. Moreover, it can be appreciated that when the interior annular groove 420 is received over the annular protrusion 422, the feed portion 413 is snap fit onto the elongated body 414 to provide tactile feedback to the user that the feed portion 413 is fully received on the elongated body 414.

The cap portion 416 may be any suitable cross-sectional shape, however, it is preferably substantially circular in cross section to define a smooth extension of the elongated body 414. The elongated body 414 may somewhat increase in cross-sectional diameter toward the upper end of the elongated body 414 to define a cap transition portion 444. The cap transition portion 444 intersects an upper, cap receiving portion 442 that is smaller in cross-sectional diameter (e.g., substantially the same cross-sectional diameter and the remainder of the elongated body 414). The cap receiving portion 442 includes the annular protrusion 422 that is received within the annular groove 420 of the cap portion 416. The cap receiving portion 442 and cap transition portion 444 are preferably of a predetermined cross-sectional diameter such that when the cap portion 416 is received on the cap receiving portion 442, the outer surface of the cap portion 416 is substantially flush with the outer surface of the elongated body 414 to define a substantially smooth transition therebetween.

Turning back to the description of the feed portion 413, the cap portion 416 extends upwardly away from the upper end of the elongated body 414 and curves inwardly to define a feed portion opening 17 in substantially the center of the feed portion 413. A hollow nozzle receiving portion 424 extends downwardly from the feed portion opening 417 into the upper, open end of the elongated body 414. The nozzle receiving portion 424 is preferably a continuation of the cap portion 416 transitioning into the feed portion opening 417, and it is in fluid communication with the feed portion opening 417. In other words, the feed portion 413, defined by the cap portion 416, the feed portion opening 417, and the nozzle receiving portion 424, is preferably a unitary, integral, homogenous structure formed by injection molding or another suitable method.

The nozzle receiving portion 424 preferably tapers as it extends downwardly from the feed portion opening 417 into the upper open end of the elongated body 414. As such, the interior cross-sectional diameter of the nozzle receiving portion 424 decreases as the nozzle receiving portion 424 extends from the feed portion opening 417 into the upper open end of the elongated body 414. The nozzle receiving portion 424 is of a suitable length and predetermined, decreasing cross-sectional diameter such that when a nozzle 38 of a prepackaged enema 412 is received within the nozzle receiving portion 424, the distal end of the nozzle 38 is tightly received within the nozzle receiving portion 424. In this manner, the nozzle 38 may be easily inserted into the feed portion opening 417 and can extend downwardly into the nozzle receiving portion 424 to form a tight fit therebetween. The interference of the nozzle receiving portion 424 and the nozzle 38 thereby creates a substantially fluid-tight seal between the nozzle 38 and the nozzle receiving portion 424. As such, when fluid is squeezed out of the bottle 32 of the prepackaged enema 12 and into the nozzle 38, the fluid travels downwardly into the nozzle receiving portion 424 without any fluid leaking upwardly and outwardly from the feed portion 413.

The distal end of nozzle receiving portion 424 terminates in a tube opening 426 that may be placed into fluid communication with a fluid channel, or transport tube 418. The transport tube 418 is receivable over the distal end of nozzle receiving portion 424 to place the transport tube 418 into fluid communication with the nozzle receiving portion 424. The transport tube 418 is preferably made from a suitably flexible, deformable material, such as plastic, rubber, etc., such that it may be stretched to fit over the distal end of nozzle receiving portion 424. For instance, in the preferred embodiment, the transport tube 418 is made from readily available clear vinyl tubing. Barbed projections 448 may be formed on the exterior of the distal end of nozzle receiving portion 424 to help secure the transport tube 418 thereon.

The transport tube 418 extends from the distal end of the nozzle receiving portion 424 throughout the length of the elongated body 414. The interior cross-sectional diameter of the elongated body 414 may be substantially the same size or larger than the cross-sectional diameter of the transport tube 418 such that the transport tube 418 may be received therein. In the depicted embodiment, the interior cross-sectional diameter of the elongated body 414 is larger than the cross-sectional diameter of the transport tube 418. Moreover, first and second annular protrusions 450 and 450 are formed on the interior of the elongated body 418 near each end of the elongated body 418. The first and second annular protrusions 450 and 450 define openings that are substantially the same cross-sectional diameter as the transport tube 418 such that the transport tube 418 is securely received therein. In this manner, the transport tube 418 is substantially maintained in its position when received within the elongated body 418.

It should be appreciated that the elongated body 418 may instead define a central, elongated opening that is placed into direct fluid communication with the nozzle receiving portion 424 to transport fluid within the elongated body 418 without the use of a transport tube 418. In this case, the central, elongated opening in the elongated body 418 would be considered the "channel" or "transport tube." Thus, the description and illustrations provided herein should not be construed as limiting the scope of the claimed subject matter.

The opposite end of the transport tube 418 is coupled to a discharge portion 428 secured to the lower, distal, curved end of the elongated body 414. The discharge portion 428 includes a cap portion 454 secured to the distal end of the elongated body 414 in substantially the same manner described above with respect to the feed portion 413. Thus, for the sake of brevity, the detailed description of the cap portion 454 and how it mounts to the elongated body 414 will not be hereinafter provided.

The cap portion 454 of the discharge portion 428 extends upwardly away from the distal end of the elongated body 414 toward a discharge opening 430 formed in substantially the center of the discharge portion 428. The discharge portion 428 is preferably contoured around the discharge opening 430 such that it is adapted to position the enema device 10 against the buttocks of the patient A for application of the enema. Preferably, the discharge portion 428 is contoured to help align the discharge opening 430 against the patient's rectum and provide comfort to the patient A during use.

Any suitable discharge portion 428 shape and contour may be used. For instance, the shape and contour of the discharge portion 428 may be similar to any one of the embodiments shown and described above with respect to FIGS. 1-5. In the embodiment depicted in FIGS. 7 and 8, the discharge portion 428 includes a self-centering upward protrusion 458 formed around the discharge opening 430 that is substantially similar to the self-centering protrusion 42 described above with respect to the enema device 10. The self-centering upward protrusion 458 may be any suitable contoured shape to engage the opening of the rectum.

The discharge portion 428 further includes a tube-engaging portion 462 extending downwardly from the discharge opening 430 and in fluid communication therewith. The tube-engaging portion 462 may taper as it extends downwardly from the discharge opening 430 toward the transport tube 418. The distal end of the tube-engaging portion 462 is coupled to the transport tube 418 in a substantially similar manner as that described above with respect to the nozzle receiving portion 424 of the feed portion 413. The components of the discharge portion (i.e, the tube-engaging portion 462 and the cap portion 454) are preferably a unitary, integral, homogenous structure formed by injection molding or another suitable method.

It should be appreciated that although the enema device 410 is described above as having an elongated body 414 connectable to a feed portion 413 and a discharge portion 428, the elongated body 414, feed portion 413, and discharge portion 428 may instead be formed as one, integral unit.

Referring to FIG. 7, the enema device 410 may be used with a prepackaged disposable enema 12 or any other suitable enema in substantially the same manner as that described above with respect to the enema device 10. More specifically, the enema device 410 is most easily used when the patient A is seated on a toilet B. To use the enema device 410, the patient A positions the discharge portion 428 beneath his or her buttocks such that an upper portion of the elongated body 414 and the feed portion 413 extend upwardly and outwardly from the toilet B in front of the patient A. The patient A then positions the discharge portion 428 properly against the rectum such that the self-centering protrusion 458 is received therein and the opening 430 is in fluid communication therewith.

The patient A thereafter pushes the upper portion of the elongated body 414 outwardly to engage the elongated body 414 on the front interior portion C of the toilet B and pivot the elongated body 414 on the front interior portion C. The upper portion of the elongated body 414 is pushed outwardly until the discharge portion 428 is firmly engaged against the rectum to form a compression fit between the discharge portion 428 and the patient's buttocks without requiring insertion of the discharge portion into the rectum. While holding the enema device 410 in this position, the patient inserts the nozzle 38 of the prepackaged enema 12 into the feed portion opening 417 until the nozzle 38 is tightly received within the nozzle receiving portion 424 (see FIG. 8). The patient A then squeezes the bottle 32 of the prepackaged enema to force the medicated fluid out of the nozzle 38 and into the transport tube 418.

The fluid travels forcibly down through the transport tube 418 until it reaches the discharge opening 430 in the discharge portion 428. The medicated fluid exits the discharge opening 430 and projects upwardly into the patient's rectum. In this manner, the patient is able to administer an enema without the help of another person, and without inserting an uncomfortable tip into the rectum. However, it should be appreciated that the enema device 410 may instead be used with the assistance of a second person.

Moreover, as noted above, the enema device 410 may instead be effectively used when the patient A is standing or sitting on something that does not have an abutment device (such as the front interior portion of the toilet). For instance, if the patient is standing or sitting on something that does not have an abutment device, the patient may instead position the discharge portion 428 beneath his or her buttocks such that an upper portion of the elongated body 414 and the feed portion 413 extend upwardly and outwardly in front of the patient A. The patient A then positions the discharge portion 428 properly against the rectum such that the self-centering protrusion 458 is received therein and the opening 430 is in fluid communication therewith.

The patient A (or someone assisting the patient A) thereafter pulls substantially upwardly on the upper portion of the elongated body 414 to firmly engage the discharge portion 428 against the rectum to form a compression fit therebetween without requiring insertion of the discharge portion into the rectum. While holding the enema device 410 in this position, the patient inserts the nozzle 38 of the prepackaged enema 12 into the feed portion opening 417 until the nozzle 38 is tightly received within the nozzle receiving portion 424 (see FIG. 8). The patient A then squeezes the bottle 32 of the prepackaged enema to force the medicated fluid out of the nozzle 38, into the transport tube 418, out the discharge opening, and into the patient's rectum.

While the preferred embodiment has been illustrated and described, it will be appreciated that various changes can be made therein without departing from the spirit and scope of the present disclosure.

The embodiments of the present disclosure in which an exclusive property or privilege is claimed are defined as follows:

1. An enema device for use with a source of enema fluid having an elongated nozzle, the enema device comprising:

(a) a hollow elongated rigid body having curved unibody construction and having first and second ends and an interior extending between the first and second ends;

(b) a feed portion formed at the first end of the hollow elongated body that defines a feed portion opening, the feed portion further including a hollow nozzle receiving portion extending from the feed portion opening to a tube opening and in fluid communication with both the feed portion opening and the interior of the hollow elongated body, the hollow nozzle receiving portion sized and configured to longitudinally slidably receive an elongated nozzle of a source of enema fluid, wherein when the elongated nozzle is longitudinally slidably received within the hollow nozzle receiving portion, the elongated nozzle is in fluid communication with the interior of the hollow elongated body, and wherein the interior of the hollow nozzle receiving portion is tapered, decreasing in cross-sectional area as it extends from the proximal end of the feed portion opening towards the tube opening and the interior of the hollow elongated body, and wherein the tapered hollow nozzle receiving portion is configured to form a fluid-tight seal between the hollow nozzle receiving portion and the received elongated nozzle of the source of enema fluid;

(c) a discharge portion disposed at the second end of the elongated body, the discharge portion defining a discharge opening in communication with the interior of the hollow elongated body; and (d) a tube extending from the nozzle receiving portion, through the interior of the hollow elongated body, to the discharge portion, wherein the tube is supported and immobilized by a first annular protrusion formed on the interior of the hollow elongated body.

2. The enema device of claim 1, wherein the discharge portion is suitably sized and contoured to engage a patient's buttocks and align the discharge opening with the patient's rectum without being inserted into the patient's rectum.

3. The enema device of claim 1, wherein the discharge portion defines a self-centering protrusion formed around the discharge opening.

4. The enema device of claim 1, wherein a first end of the tube is receivable on the nozzle receiving portion.

5. The enema device of claim 1, wherein the discharge portion further comprises a tube-engaging portion in fluid communication with the discharge opening and extending from the discharge opening.

6. The enema device of claim 5, wherein the tube-engaging portion is receivable within a second end of the tube.

7. The enema device of claim 1, wherein the feed portion further comprises a cap portion selectively engageable with the first end of the hollow elongated body.

8. The enema device of claim 1, wherein the tube is flexible.

9. The enema device of claim 1, further comprising a second annular protrusion that supports and immobilizes the tube, wherein said second annular protrusion is intermediate the first annular protrusion and the second end of the tube.

10. The enema device of claim 1, wherein the tube is sized and configured to transport enema fluid from the feed portion to the discharge portion.

11. The enema device of claim 1, wherein the tube has an outer diameter that is smaller than an inner diameter of the hollow elongated rigid body.

* * * * *